United States Patent [19]

Buendia et al.

[11] 3,984,442
[45] Oct. 5, 1976

[54] PROCESS FOR THE PREPARATION OF TRANS-EPOXY CIS-ALKENES

[75] Inventors: Jean Buendia, Nogent-sur-Marne; Michel Vivat, Lagny-sur-Marne, both of France

[73] Assignee: Roussel-UCLAF, Paris, France

[22] Filed: Aug. 15, 1975

[21] Appl. No.: 605,159

[30] Foreign Application Priority Data

Sept. 18, 1974 France .............................. 74.31500

[52] U.S. Cl. ............................................ 260/348.6
[51] Int. Cl.² ....................................... C07D 303/14
[58] Field of Search ...................... 260/348.6, 348 R Primary Examiner—Norma S. Milestone
Attorney, Agent, or Firm—Hammond & Littell

[57] ABSTRACT

A novel process for the preparation of substituted trans-epoxy cis-alkenes of the formula

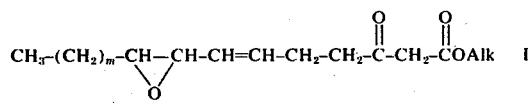

wherein Alk is straight or branched alkyl of 1 to 6 carbon atoms and $m$ is 3, 4 or 5 which are intermediates for prostaglandin compounds.

10 Claims, No Drawings

PROCESS FOR THE PREPARATION OF TRANS-EPOXY CIS-ALKENES

STATE OF THE ART

Commonly assigned U.S. Pat. No. 3,736,319 describes the production of trans-epoxy cis-alkenes of formula I by reacting propargylacetic acid or a derivative thereof with a precursor agent for alkyl acetate to form alkyl 3-oxo-6-heptynoate of the formula

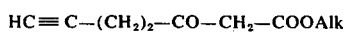   II wherein Alk is alkyl of 1 to 7 carbon atoms, reacting the latter with an etherification agent to form alkyl 3-alkoxy-6-yne-2-heptenoate of the formula

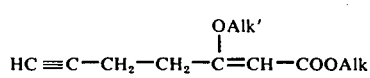   III wherein Alk' is alkyl of 1 to 7 carbon atoms, condensing the latter in the form of a metallic salt with an α-halo-alkanal of the formula

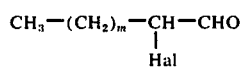   IV wherein Hal is bromine or chlorine and m is 3,4 or 5 to form an alkyl 3-alkoxy-8-hydroxy-9-halo-6-yne-2-alkenoate of the formula

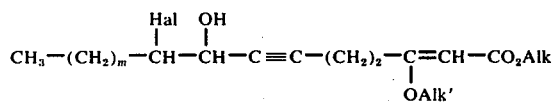

hydrolyzing the latter with an acid agent to form alkyl 3-oxo-8-hydroxy-9-halo-6-alkynoate of the formula

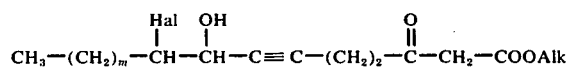

hydrogenating the latter in the presence of a partially deactivated metallic catalyst to form alkyl 3-oxo-8-hydroxy-9-halo-cis 6-alkenoate of the formula

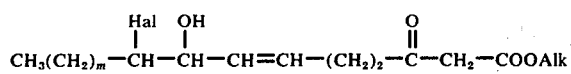   VII and reacting the latter with an alkali metal alcoholate to form a trans epoxy-cis alkene of the formula

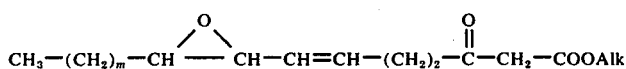   I

OBJECTS OF THE INVENTION

It is an object of the invention to provide a novel process for the preparation of trans-epoxy cis-alkenes of formula I.

It is another object of the invention to provide novel intermediates of the formula

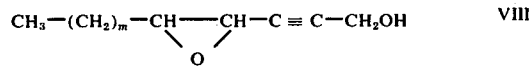   VIII wherein m is 3,4 or 5.

These and other objects and advantages of the invention will become obvious from the following detailed description.

THE INVENTION

The novel process of the invention for the preparation of trans-epoxy cis-alkenes of the formula

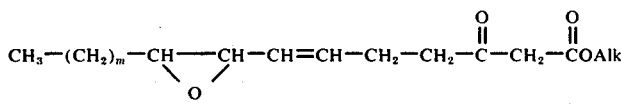   I wherein Alk is alkyl of 1 to 6 carbon atoms and m is 3,4 or 5 comprises reacting an α-halo-alkanal of the formula

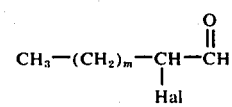   IX wherein m is 3,4 or 5 and Hal is chlorine or bromine with a metallic derivative of the acetylenic group of propargyl alcohol to obtain a compound of the formula

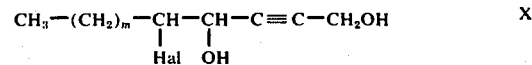   X reacting the latter with an alkaline agent to obtain a compound of the formula

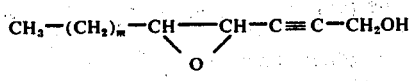 XI reacting the latter with a halogenation agent to obtain a compound of the formula

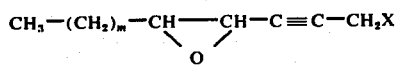 XII wherein X is bromine or chlorine, reacting the latter with a dianion of a compound of the formula

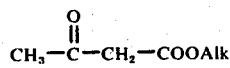 XIII wherein Alk has the above definition, this dianion being formed with the aid of alkaline agents, to obtain a compound of the formula

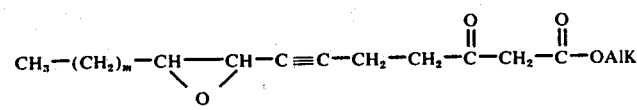 XIV and reacting the latter with hydrogen in the presence of a partially deactivated metal catalyst to obtain the corresponding compound of formula I.

Among the groups of Alk are methyl, ethyl, propyl, isopropyl, butyl, tert.-butyl, pentyl, isopentyl and hexyl.

A particularly preferred portion of the invention for the preparation of compounds of formula I is the reaction of a compound of formula XII with a dianion of a compound of formula XIII to obtain a dianion which is treated with an alkaline agent to obtain a compound of formula XIV which is then hydrogenated in the presence of a partially deactivated metal catalyst to form the corresponding compound of formula I.

The metallic derivative of propargyl alcohol for reaction with the α-halo-alkanal of formula IX is preferably the organo magnesium derivative formed by reaction of ethyl magnesium bromide with propargyl alcohol but other metal derivatives of the acetylenic group such as lithium, potassium, or sodium may also be used.

The alkaline agent to change the halohydrin group of the compound of formula X into the epoxy group is preferably potassium tert.-butylate but other alkali metal alcoholates or alkali metal amides or alkali metal hydrides may also be used.

The halogenation agent for reaction with the compound of formula XI is preferably carbon tetrachloride or carbon tetrabromide in the presence of triphenylphosphine but other agents such as phosphorus trichloride or phosphorus tribromide in the presence of pyridine are also useful.

The alkaline agents used to form the dianion of the compound of formula XIII is preferably sodium hydride and butyllithium but other reagents such as sodium amide and lithium diethylamide or diidopropylamide or butyllithium, sodium hydride and methyl lithium may also be used.

The hydrogenation catalyst is preferably palladium on barium sulfate partially deactivated by the presence of quinoline but other catalysts such as palladium on calcium carbonate partially deactivated by lead acetate addition or Raney nickel may also be used.

In a preferred embodiment of the process of the invention, ethyl 3-oxo-trans 8,9-epoxy-cis-6-tetradecenoate is prepared by reacting an organo magnesium derivative of propargyl alcohol with α-chloro-heptanal to form 5-chloro-4-hydroxy-2-decynol, reacting the latter with potassium tert.-butylate to form trans 4,5-epoxy-2-decynol, reacting the latter with carbon tetrabromide in the presence of triphenylphosphine to form 1-bromo-trans 4,5-epoxy-2-decyne, reacting the latter with the dianion of ethyl acetylacetate, formed by reacting of sodium hydride and butyllithium to form ethyl trans-8,9-epoxy-3-oxo-6-tetradecynoate and reacting the latter with hydrogen in the presence of palladium on barium sulfate partially deactivated by quinoline to obtain ethyl 3-oxo-trans 8,9-epoxy-cis-6-tetradecenoate.

The compounds of formula I are known to be intermediates for the preparation of prostaglandin compounds as described in French Pat. No. 2,085,652. The process of the invention has the advantage over known processes for the preparation of compounds of formula I since the individual steps of the process are simpler with more satisfactory yields for each step. The compounds of formula VIII are novel and a part of the invention.

In the following example there are described several preferred embodiments to illustrate the invention. However, it should be understood that the invention is not intended to be limited to the specific embodiments.

EXAMPLE ethyl 3-oxo-trans 8,9-epoxy-cis-6-tetradecenoate

STEP A: 5-chloro-4-hydroxy-2-decynol 460 ml of a solution of ethyl magnesium bromide in tetrahydrofuran titrating 0.71 moles per liter were added dropwise to a solution of 9 g of propargyl alcohol in 100 ml of tetrahydrofuran and after stirring the mixture for 1½ hours, a solution of 35.6 g of α-chloro-heptanal in 100 ml of tetrahydrofuran was added thereto. The mixture was stirred for one hour and was then poured into a saturated aqueous monosodium phosphate solution. The mixture was extracted with ether and the organic phase was washed with water, dried over magnesium sulfate and evaporated to dryness under reduced pressure at 100°C. The residue was chromatographed over silica gel and was eluted with a 4-1 benzene-ethyl acetate mixture to obtain 16.6 g of 5-chloro-4-hydroxy-2-decynol in the form of a yellow oil.

Analysis: $C_{10}H_{17}ClO_2$ Calculated: %C, 58.68; %H, 8.31; %Cl, 17.36. Found: %C, 58.7; %H, 8.2; %Cl, 16.9.

STEP B: trans 4,5-epoxy-2-decynol 102 ml of a solution of potassium tert.-butylate in tetrahydrofuran titrating 0.9 moles per liter were added dropwise to a solution of 9.4 g of 5-chloro-4-hydroxy-2- decynol in 94 ml of tetrahydrofuran cooled to 0°C and the mixture was stirred for 20 minutes and then poured into a saturated aqueous monosodium phosphate. The mixture was extracted with ethyl acetate and the organic phase was washed with a saturated aqueous sodium chloride solution, dried over magnesium sulfate and evaporated to dryness to obtain 7.75 g of trans 4,5-epoxy-2-decynol in the form of a yellow oil used as is for the next step. Thin-layer chromatography (silica gel — 1:1-cyclohexane-ethyl acetate eluant) had an Rf = 0.53.

Analysis: $C_{10}H_{16}O_2$. Calculated: %C, 71.42; %H, 9.51. Found: %C, 71.1; %H, 9.7.

STEP C: 1-bromo-trans 4,5-epoxy-2-decyne 12.3 g of triphenylphosphine were added portion wise to a mixture of 5.26 g of the product of Step B, 16 g of carbon tetrabromide and 100 ml of methylene chloride maintained at 26°C and after the addition was complete, the solvent was evaporated under reduced pressure. The residue was triturated with hexane and the mixture was filtered. The filtrate was evaporated to dryness and the residue was chromatographed over silica gel. Elution with a 9-1 cyclohexane-ethyl acetate mixture yielded 5 g of 1-bromo-trans 4,5-epoxy-2-decyne in the form of a yellow oil. Thin-layer chromatography (silica gel — 9-1 cyclohexane-ethyl acetate eluant) showed an Rf = 0.5

STEP D: ethyl trans 8,9-epoxy-3-oxo-6-tetradecynoate

A solution of 3.224 g of ethyl acetylacetate in 5 ml of tetrahydrofuran was added dropwise to a suspension of 1.19 g of a 50% sodium hydride in mineral oil in 40 ml of tetrahydrofuran cooled to 0°C and after stirring the mixture at 0°C for 1 hour, 15.5 ml of a solution of butyllithium in tetrahydrofuran titrating 1.6 moles per liter were added to the reaction solution. The mixture was stirred for 45 minutes and was then cooled to −60°C after which a solution of 5.718 g of 1-bromo-trans 4,5-epoxy-2-decyne in 5 ml of tetrahydrofuran were added thereto. The mixture stood at −60°C for one hour and was then poured into an iced aqueous solution saturated with mono sodium phosphate. The mixture was extracted with ethyl acetate and the organic phase was evaporated to dryness under reduced pressure at 40°C. The residue was chromatographed over silica gel and was eluted with a 9-1 cyclohexane-ethyl acetate mixture to obtain 4 g of ethyl trans 8,9-epoxy-3-oxo-6-tetradecynoate in the form of a yellow oil. Thin-layer chromatography [silica gel — 9-1 cyclohexane-ethyl acetate] showed an Rf = 0.25.

STEP E: ethyl 3-oxo-trans 8,9-epoxy-cis-6-tetradecenoate

A mixture of 560 mg of the product of Step D, 100 mg of barium sulfate containing 5.25% of palladium, 5 ml of ethyl acetate and 0.05 ml of quinoline was stirred at −10°C in a hydrogen atmosphere until the theoretical quantity of hydrogen had been absorbed and the mixture was filtered to remove the catalyst. The filtrate was neutralized at 0°C with N hydrochloric acid and was evaporated to dryness under reduced pressure. The residue was chromatographed over silica gel and was eluted with a 1-1 cyclohexane-ethyl acetate mixture to obtain 363 mg of ethyl 3-oxo-trans 8,9-epoxy-cis-6-tetradecenoate in the form of a yellow oil. Thin-layer chromatography [silica gel — 1-1 cyclohexane-ethyl acetate] showed an Rf = 0.6.

Various modifications of the products and process of the invention may be made without departing from the spirit or scope thereof and it should be understood that the invention is intended to be limited only as defined in the appended claims.

We claim:

1. A process for the preparation of a compound of the formula

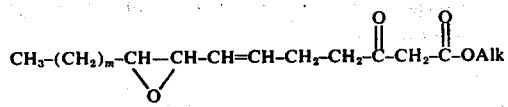

wherein m is 3,4 or 5 and Alk is alkyl of 1 to 6 carbon atoms comprising reacting an α-halo-alkanal of the formula

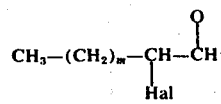

wherein m is 3,4 or 5 and Hal is chlorine or bromine with a metallic derivative of the acetylenic group of propargyl alcohol to obtain a compound of the formula

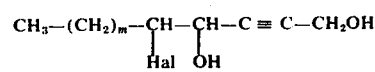

reacting the latter with an alkaline agent to obtain a compound of the formula

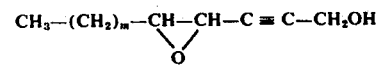

reacting the latter with a halogenation agent to obtain a compound of the formula

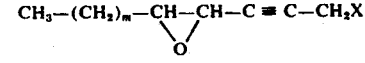

wherein X is bromine or chlorine, reacting the latter with a dianion of a compound of the formula

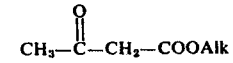

wherein Alk has the above definition, this dianion being formed with the aid of alkaline agents, to obtain a compound of the formula

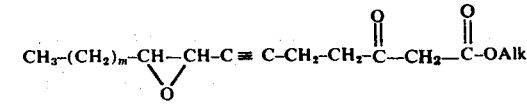

and reacting the latter with hydrogen in the presence of a partially deactivated metal catalyst to obtain the corresponding compound of the desired formula.

2. The process of claim 1 wherein the propargyl alcohol derivative is a magnesium derivative.

3. The process of claim 1 wherein the alkaline agent is potassium tert.-butylate.

4. The process of claim 1 wherein the halogenation agent is carbon tetrabromide or carbon tetrachloride.

5. The process of claim 1 wherein the dianion is formed with sodium hydride and butyllithium.

6. The process of claim 1 wherein the catalyst is palladium on barium sulfate partially deactivated with quinoline.

7. A process for the preparation of a compound of the formula

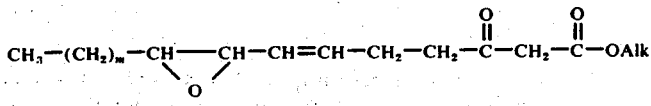

wherein $m$ is 3,4 or 5 and Alk is alkyl of 1 to 6 carbon atoms comprising reacting a compound of the formula

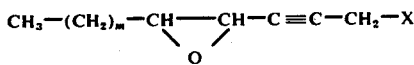

wherein $m$ is 3,4 or 5 and X is chlorine or bromine with a dianion of a compound of the formula

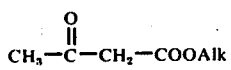

to form a compound of the formula

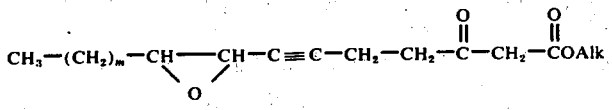

and reacting the latter with hydrogen in the presence of a partially deactivated metal catalyst to form the desired compound.

8. A process for the preparation of a compound of the formula

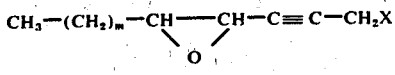

wherein $m$ is 3,4 or 5 and X is chlorine or bromine comprising reacting a compound of the formula

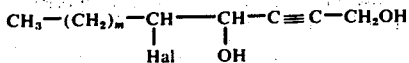

wherein $m$ is 3,4 or 5 and Hal is chlorine or bromine with an alkaline agent to obtain a compound of the formula

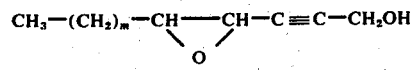

and reacting the latter with a halogenation agent to obtain the desired halogenated compound.

9. A process for the preparation of a compound of the formula

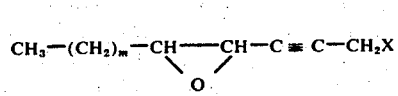

wherein $m$ is 3, 4 or 5 and X is bromine or chlorine comprising reacting an α-halo-alkanal of the formula

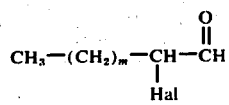

wherein Hal is chlorine or bromine with a metallic derivative of the acetylenic group of propargyl alcohol to obtain a compound of the formula

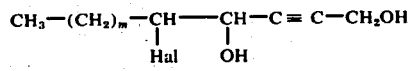

reacting the latter with an alkaline agent to obtain a compound of the formula

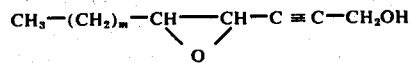

reacting the latter with a halogenation agent to obtain the desired halogenated compound.

10. A compound of the formula

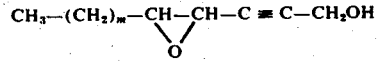

wherein $m$ is 3, 4 or 5.

* * * * *